United States Patent
LePage (10) Patent No.: US 9,316,618 B2
(45) Date of Patent: Apr. 19, 2016

(54) METHOD FOR MONITORING THE INTEGRITY OF AN EDDY CURRENT INSPECTION CHANNEL

(71) Applicant: Benoit LePage, Ancienne-Lorette (CA)

(72) Inventor: Benoit LePage, Ancienne-Lorette (CA)

(73) Assignee: OLYMPUS NDT, INC., Waltham, MA (US)

( * ) Notice: Subject to any disclaimer, the term of this patent is extended or adjusted under 35 U.S.C. 154(b) by 88 days.

(21) Appl. No.: 14/226,105

(22) Filed: Mar. 26, 2014

(65) Prior Publication Data

US 2015/0276679 A1 Oct. 1, 2015

(51) Int. Cl.
 *G01R 33/12* (2006.01)
 *G01N 27/90* (2006.01)
(52) U.S. Cl.
 CPC ............ *G01N 27/90* (2013.01); *G01N 27/9033* (2013.01)
(58) Field of Classification Search
 CPC ...... G01R 33/12; G01R 33/028; G01N 27/90; G01N 27/9046; G01N 27/9006; G01N 27/902; G01N 27/82; G01N 27/83
 See application file for complete search history.

(56) References Cited

U.S. PATENT DOCUMENTS 5,019,777 A * 5/1991 Gulliver et al. ............... 324/242
2012/0019236 A1* 1/2012 Tiernan et al. ................ 324/234

FOREIGN PATENT DOCUMENTS

JP 62186392 A * 8/1987 ............ G06K 17/00

* cited by examiner

*Primary Examiner* — Son Le
(74) *Attorney, Agent, or Firm* — Ostrolenk Faber LLP (57) ABSTRACT

An eddy current object testing system includes an EC probe and an acquisition channel which is configured to receive an EC signal from the EC probe and to generate a visual output, namely an impedance plane representation, of the output. A display is coupled to the acquisition channel to display the visual output. The at least one probe is provided with a test loop substantially surrounding it and has a series switch which can be selectively closed or opened to thereby cause the image plane to assume a state that is indicative of a fault, if any, in the EC probe.

18 Claims, 7 Drawing Sheets

METHOD FOR MONITORING THE INTEGRITY OF AN EDDY CURRENT INSPECTION CHANNEL

FIELD OF THE INVENTION

The present invention relates to non-destructive testing and inspection systems (NDT/NDI) and, more particularly, to Eddy Current (EC) or Eddy Current Array technology (ECA), employing eddy current probes with a test loop linked to it, which allows checking the integrity of the testing system.

BACKGROUND OF THE INVENTION

Eddy current inspection is commonly used as a non-destructive method to detect flaws in surfaces of manufactured components fabricated from a conductive material, such as bars, tubes, and special parts for automotive, aeronautic or energy industries.

Typical eddy current sensor configurations are impedance bridge, pitch-catch (alternatively called reflection or transmit-receive) and differential, but can also include more complex combinations such as pitch-catch with differential receivers, multi-differential, etc.

Each eddy current system regardless of its configuration is composed of coils in different shapes. In a standard eddy current testing, a circular coil carrying current is placed in proximity to the test specimen (which must be electrically conductive). The alternating current in the coil generates a changing magnetic field, which interacts with the test specimen and generates eddy currents. Variations in the phase and magnitude of these eddy currents can be monitored using a receiver coil, or by measuring changes to the current flowing in the primary driver coil. Variations in the electrical conductivity or magnetic permeability of the test object, or the presence of any flaws, will cause a change in eddy current and a corresponding change in the phase and amplitude of the measured current.

Eddy current field conditions associated with problematic component conditions (including flaws, conductivity variation, thickness, etc) can then lead to non-destructive examination of the component.

It is always interesting to determine or verify the correct functioning of the eddy current inspection systems; including the entire system acquisition chain, the driver and receiver arrangement, especially when there is an eddy current array with different numbers of coils which makes it difficult to find the broken coils in the system. Since non-destructive testing is typically achieved on critical components, the ability to confirm the correct operation of the inspection system does have a direct impact of the safety level of the inspected component by elimination of risks associated with inspection system malfunctions.

Determining the whole system acquisition chain functionality is especially important and interesting between the inspections. This ensures the correct functioning of inspection system. An integrity check method should be capable of producing a system condition diagnostic in between consecutive inspections of a bar, for example in order to validate that a whole batch of bars has been inspected with a functional system and also to raise an alarm as soon as a failure in the testing equipment is detected.

Determining the probe functionality has been under investigation for many years and there are patented inventions in this field.

U.S. Pat. No. 8,395,377 describes a system for determining the correct functioning of an eddy current probe/cable system. According to that patent, the determination of the status is based on a frequency of the eddy current probe oscillator. The method comprises a plurality of steps. In a first step, a frequency of the eddy current probe oscillator is measured. In a second step, the measured frequency is compared to one or more previously measured frequencies, and/or to a predefined frequency, and/or to a predefined range of frequencies. In a third step, the status is determined by means of the result of the frequency comparison. In another embodiment, the amplitude of the demodulated frequency is measured and compared to one or more previously measured amplitudes, and/or to predefined amplitude, and/or to a predefined range of amplitudes. And that third step of determining the status also comprises determining the status by means of the result of the amplitude comparison.

Although the known method allows determining the correct functioning of the eddy current system, there are some limitations, which restrict the application of this method. First of all, this invention checks only the probe functionality and not the whole acquisition chain. Moreover, the invention needs dedicated probe checking electronics. In addition, the patented method may become difficult to apply to a complex probe design, which includes a multiple coil array.

Another patent (U.S. Pat. No. 8,421,471) describes a self-test unit linked to an eddy current system which performs systematic quantitative checking of the signal processing functions of the signal processing unit, the transmitting coil arrangement, and the receiver coil arrangement, and upon request, calibrates the signal processing unit with a calibration standard which is to replace the transmitter coil arrangement and/or the receiver coil arrangement.

The U.S. Pat. No. 8,421,471 patent asserts that this is advantageous because it allows for comprehensive checking of the functions of the front-end, especially of the filters and amplifiers as well as the probe, and thus, high reliability of the measurement results is achieved, and calibration of the device is also easily enabled. This applies especially to calibration with respect to the adjustable preamplifier.

Nonetheless, the complexity of the U.S. Pat. No. 8,421,471 invention limits its applications. The method requires multiple steps including disconnecting the probe and dedicated electronic and mechanics. In addition, based on its explanation, it seems the U.S. Pat. No. 8,421,471 invention is only suitable to test impedance probes.

Thus, the known probe checking techniques partially meet the need to provide eddy current system integrity diagnostics. Still, a new technique is needed to eliminate the limitations and disadvantages of the known methods, especially for multi-element probes. In particular, there is a need for an eddy current system condition monitor that will be fast enough to be operated between consecutive inspection sequences, that will allow monitoring of the whole acquisition chain including the probe, that could be adapted for multiple probe type including eddy current array and that will be inexpensive.

The following section describes advantages of the presented invention, which eliminate the limitations and drawbacks of the known art described in the foregoing patents.

Objectives and Advantages

An objective of the present invention is to provide an ECA system integrity testing method and system that is usable between object inspection sequences, without stopping or slowing down the object testing system as a whole.

This invention has advantages over exiting integrity checking methods including the following. First of all, the technique allows testing the integrity of the entire system acquisition chain, with an ability to generate eddy currents to receive eddy current signals and to generate a proper signal and/or indication on the impedance plane.

In addition, this method can be adapted to existing eddy current or eddy current array acquisition circuitry. Simple and inexpensive implementation makes it scalable to large eddy current array systems with different types of probes and coil configurations, which specially makes it very interesting in probes with multi-element channels. The method is also extremely fast (less than 1 second) and can thus be used in the very short time intervals available between consecutive object inspections.

SUMMARY OF THE INVENTION

The invention comprises including a conductive circuit (test loop) in the probe in which the eddy current probe induces a difference of potential. This test circuit can be remotely opened and closed. Closing the circuit (the test loop) induces currents which are detected by the eddy current system, and allows for monitoring the instrumentation. Opening the circuit makes it possible to use the system for inspecting components since it then becomes non-intrusive as no eddy currents are generated in the open circuit test loop.

For checking the ECA system integrity, a programmable controller can activate the test loop, which is then seen on each of the channels as a relatively big signal change. Comparing the probe check reference signal acquired when the system works properly with the signal for the current probe check evaluation makes it possible to accurately assess the condition of the whole system as well as of individual channels of probe.

In accordance with preferred embodiments of the invention, the eddy current object testing system comprises: at least one EC probe including a drive-sense channel; at least one EC acquisition channel configured to receive an EC signal from the at least one EC probe and to generate an EC output representative of characteristics of the EC signal; at least one test loop substantially surrounding the at least one probe; and a switch mechanism in series with the at least one test loop, and configured to be selectively opened or closed, to thereby cause the visual output to assume a state that is indicative of a fault in the at least one EC probe.

The test loop can be provided integrally with the EC probe or separately from it and configured to be coupled to it. The EC output can be displayed in the form of an impedance plane or electronically provided in that form. There may be a single EC probe and a single test loop and/or a plurality of EC probes and one or more test loops therefor.

Other features and advantages of the present invention will become apparent from the following description of the invention which refers to the accompanying drawings.

DETAILED DESCRIPTION OF THE INVENTION

The test loop of the present invention is based on eddy current basics. Thus, when a shielding loop is positioned around an eddy current test coil, a signal will be induced in the loop and this signal will change the magnitude and phase of current flowing in the coil. The detection of these changes enables checking the ECA inspection system functionality.

Figure 1:
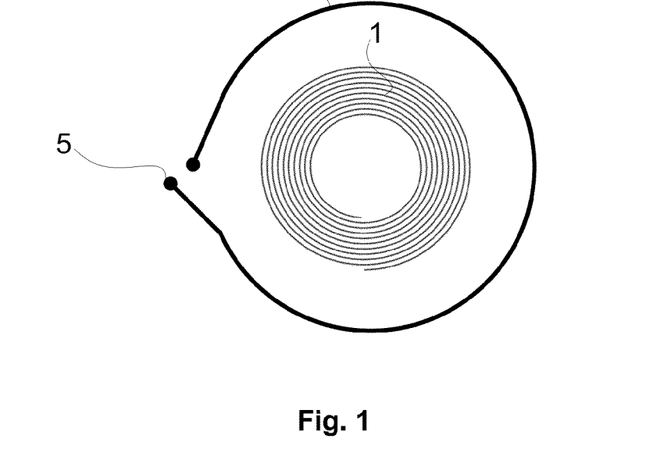
FIG. 1 shows the test loop for a simple configuration of one channel composed of one coil.

FIG. 1 is a simple configuration of the test loop in one channel, which is composed of a single coil 1, which is being used for both the generation and reception of the eddy current signals. The test loop 3 in this case consists of a conductive circuit, which turns around the inspection coil 1. The switch 5 is utilized to activate test loop 3. Once the switch 5 is closed, an eddy current is induced in the test loop 3. Consequently, the coil 1 impedance is changed. However, when the coil 1 is broken, it does not induce current in test loop 3 and consequently, shows no changes in coil's 1 impedance associated with the switch 5 position.

The electrical impedance (Z) is the total resistance that a circuit presents to an alternating current. In Eddy current circuits, impedance includes the possible resistance (R) and the inductive reactance (XL) components. The resistance component and the reactance component are not in phase, so vector addition must be used to relate them to the overall impedance. For an eddy current circuit with resistance and inductive reactance components, the total impedance is calculated using $Z=\sqrt{R^2+X_L^2}$.

Figure 2:
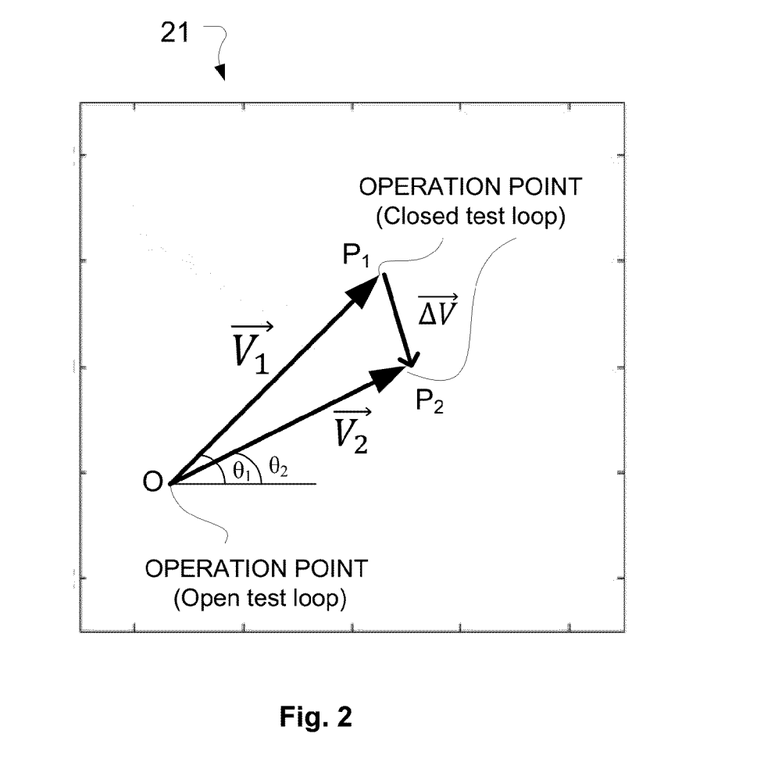
FIG. 2 illustrates the impedance plane signal associated with the activation of the test loop. This figure shows the reference test loop signal (operation point shift vector) as well as the signal associated with the current probe check evaluation.

This impedance can be graphically displayed using the impedance plane diagram 21 (FIG. 2). Impedance also has an associated angle such as $\theta_1$, called the phase angle of the circuit, which can be calculated by $$\mathrm{Tan}\theta = \frac{X_L}{R}.$$

Referring to FIG. 2, the impedance plane diagram is a very useful way of displaying eddy current inspection data. Although the exact interpretation of the displayed results is not consistently the same, depending on the probe configuration, the use of an impedance plane representation and the ability to graphically represent in-phase and out of phase components of the acquired eddy current signal has made it the accepted standard for inspections in the non-destructive testing industry. It must be understood that each acquired data correspond to a single point on the impedance plane referred as the operation point. The operation point is directly related to the global condition of the overall inspection system, the probe and the condition of the material under test. Typically, testing results based on the operation point are possible by reference to a known condition. For example, one may compare the operation point on a known good part to the operation point on an inspected component to determine or define whether the component is defective. For the operation of the test loop 3 between inspections of components, one is interested in the shift of the operation point O with the probe in the air with the test loop open and the operation point P with the probe in the air and the test loop closed.

Still referring to FIG. 2, the impedance plane is used for evaluating the results of the test loop activation (TLA). When one activates the test loop, an operation point shift will be detected in the impedance plane. This operation point shift represents changes affecting the operation point associated with closing of the test loop. The shift of the TLA operation point is a vector (such as $\vec{V_1}$ and $\vec{V_2}$). This vector is the TLA signal on which the TLA analysis will be based.

For TLA analysis it is necessary to define a reference signal which is presented here as TLA signal ($\vec{V_1}$). This reference TLA signal is obtained by activating the test loop when the whole inspection system works properly (for example after a more extensive calibration test). By comparing the reference TLA signal with the currently obtained TLA signal for the present system check evaluation ($\vec{V_2}$), one can monitor the integrity of the inspection system. In this regard, a $$\text{Probe Integrity Test Value } PITV\ (T) = \frac{|\vec{\Delta V}| = |\vec{V_1} - \vec{V_2}|}{|\vec{V_1}|}$$

is calculated which is used for system integrity tests. A threshold based on tolerance typically observed for a fully functional system is established on PITV (T). Any T readings exceeding the threshold is indicative of a system failure and produces an alarm. This and makes it possible to take appropriate action in a timely manner. At any time between the inspections, the TLA and associated PITV monitoring can be repeated.

Figure 4:
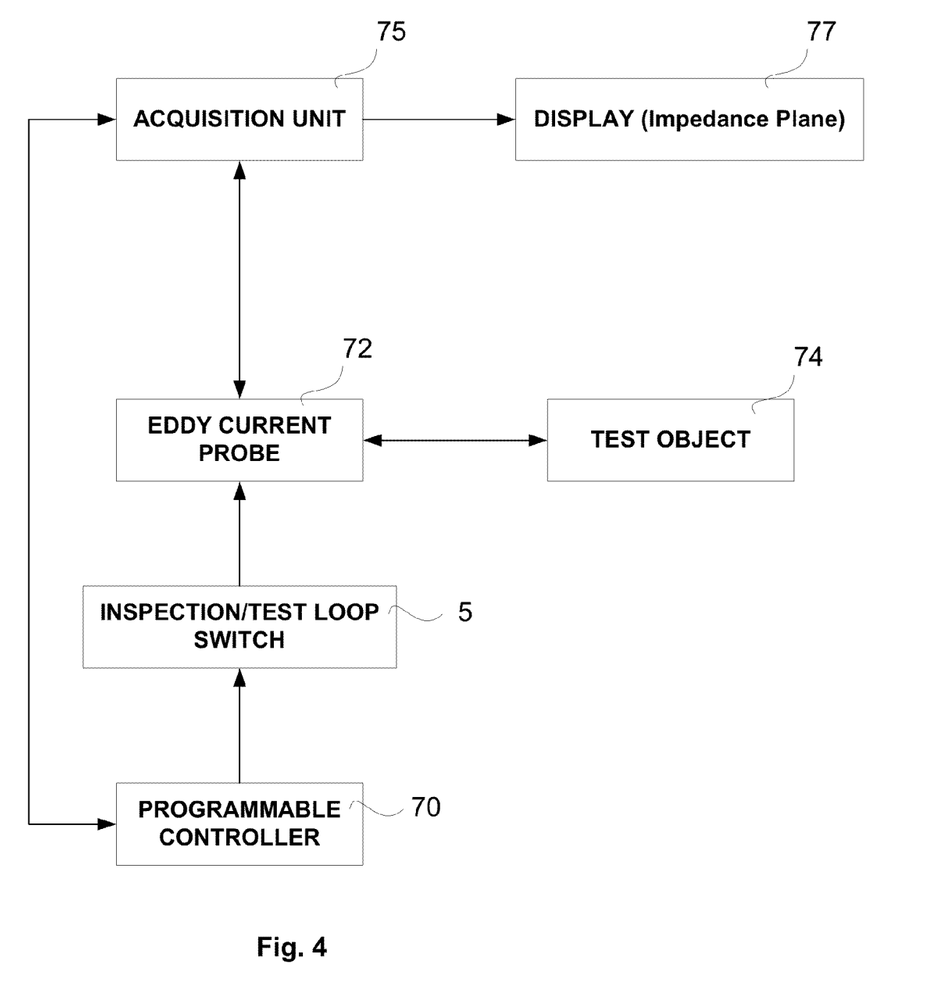
FIG. 4 shows an eddy current probe with the test loop integrated in the system. The system comprises a programmable controller, an acquisition unit and a display to show the impedance plane.

It can be appreciated that the TLA value can be calculated either by the acquisition unit 75 or the programmable controller 70, either of the embodiment is within the scope of the present disclosure.

Although the test loop shown in the drawings of the present disclosure are in a fashion of encircling the EC coils. However, the principal of the present disclosure includes all arrangements as long as the test loop intersects at least a portion of the electro-magnetic field associated to the respective drive-sense channel. This is because it is the interaction between the test loop and the electro-magnetic field of of EC channels causes the shifts in the operation points, on which the TLA calculation is based.

Figure 3A:
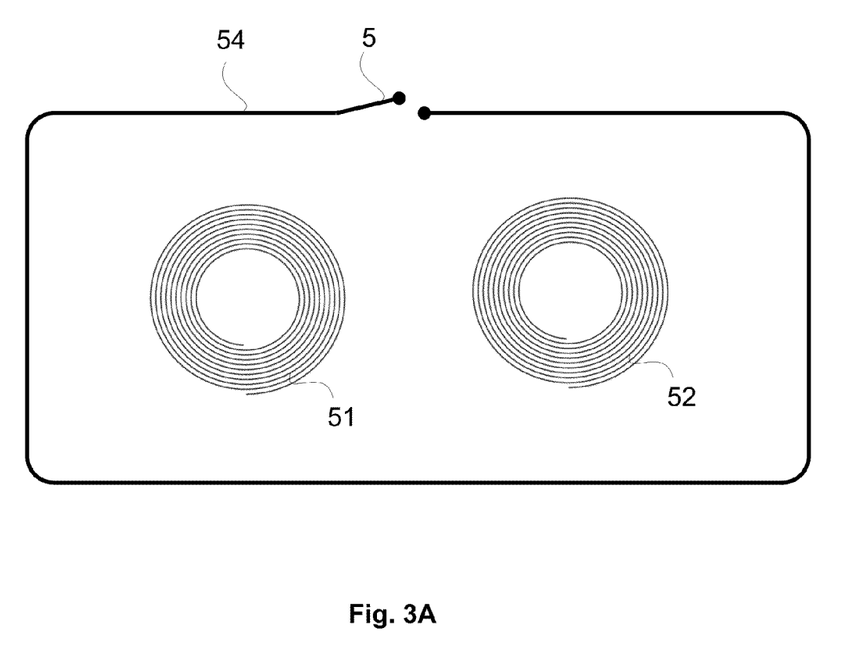
FIG. 3A shows the test loop for a pitch-catch coil configuration. Each transmitter or receiver is composed of a channel. Each channel can be composed of a different coil number and configuration.

The test loop concept can be applied to different coil configurations. FIG. 3A shows a channel composed of pitch-catch coils (transmitter coil 51, receiver coil 52). There is a test loop 54 in this configuration where the switch 5 is used to activate it. In this case, by closing the switch 5 a current will be induced in the test loop 54. Consequently, one expects to detect mutual inductance changes if the channel works properly. However, if the transmitter 51 and/or receiver 52 coils are broken, by switching to test loop, the receiver coil shows no changes. Otherwise, the principles of operation are exactly the same as for obtaining the TLA signals and the PITV monitoring.

It should be noted that the coil type can be changed in this configuration and the basics of probe checking concepts do not change.

Figure 3B:
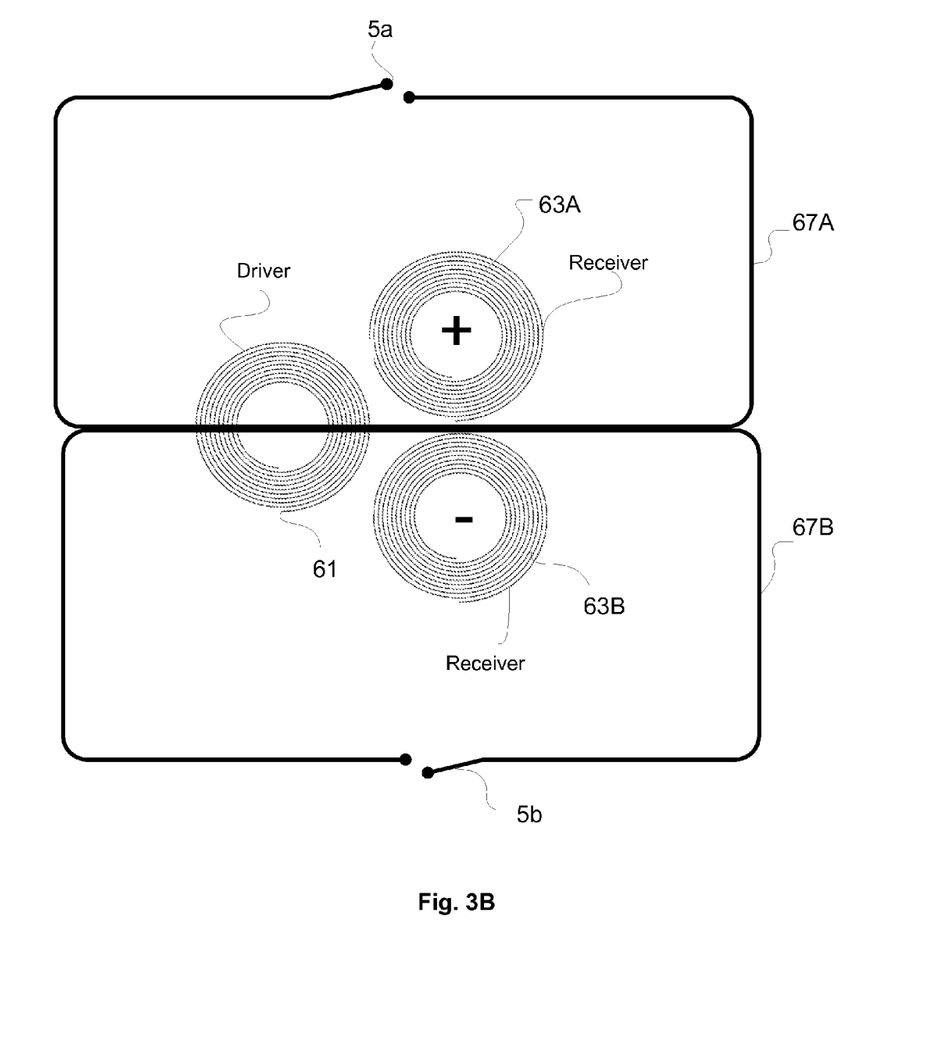
FIG. 3B shows the test loop for a differential coil configuration. Each transmitter or receiver is composed of a channel. Each channel can be composed of a different coil number and configuration.

In this regard, the probe check concept can be used for differential configurations as well (FIG. 3B). In this case the differential signal developed between the coils is measured. Differential coils are used for eliminating signals affecting simultaneously both receiver coils (example; noise associated with lift-off variations). In a probe of this type both receiver coils 63A and 63B are wound or connected in opposition. Consequently, signals that affect both receivers simultaneously cancel out. This type of configuration produces a different impedance plane trend with double indications of operation point.

Referring to FIG. 3B, a typical differential channel comprises a driver coil 61 and two receiver coils 63A and 63B. It is also possible to construct differential channels in many other ways different than the embodiment illustrated on FIG. 3B. Only one example is shown here to describe the application of the probe check concept because the solution described in association with FIG. 3B can be generalized to other differential channel configurations.

With this configuration, one needs two separate test loops (67A and 67B), each of which tests a respective, one half of the configuration as presented in FIG. 3B. Only one test loop results in the receivers' differential measurements canceling out the TLA signal.

In this case, closing switch 5a allows a current to be induced in the test loop 67A and closing switch 5b results in a current being induced in test loop 67B. Consequently, one can expect to detect operation point changes if the coils work properly by alternatively measuring the TLA signal associated with test loop 67A and 67B and generating two PITV measurements. If the driver 61 is damaged, PITV measurement associated with both receivers will be affected. If one of the receivers' 63A or 63B is damaged, the PITV associated with only this receiver will be affected.

The present invention can be integrated in an eddy current inspection system (FIG. 4) composed of different parts. This allows checking the integrity of the whole inspection system. FIG. 4 shows a schematic of the probe in a system. The programmable controller 70 allows to control the system functioning and to activate the probe test loop 80 between inspections of the test object 74. The acquisition unit 75 is used for acquisition of a signal from a test loop or from an object during the inspection test. The display 77 shows the impedance plane and measured PITV. Alternatively, the measured impedance plane value can be transferred to the programmable controller 70 in order to automatically measure PITV each time the TLA is initiated. With the system, it is possible to program and activate the test loop at any time between inspections to continually ensure the integrity of eddy current inspection system.

As shown in FIG. 4, in this invention, for the probe checking and for the object inspections the same acquisition chain (72 and 75) is used. Therefore, if any of the parts identified in FIG. 4 does not work properly, the PITV measurement will be affected enabling diagnosing the inspection system for malfunctions and the like.

The eddy current array system integrity check concept can be extended for multi-channel probes.

Depending on the probe design, these channels can be activated simultaneously or non-simultaneously in each pre-defined time interval. In each time interval, the coils comprising in the channel can be used as drivers to induce an eddy current and/or as receivers. Each channel is alternatively activated at a predetermined switching sequence and at a predetermined switching frequency during consecutive time intervals.

Figure 5A:
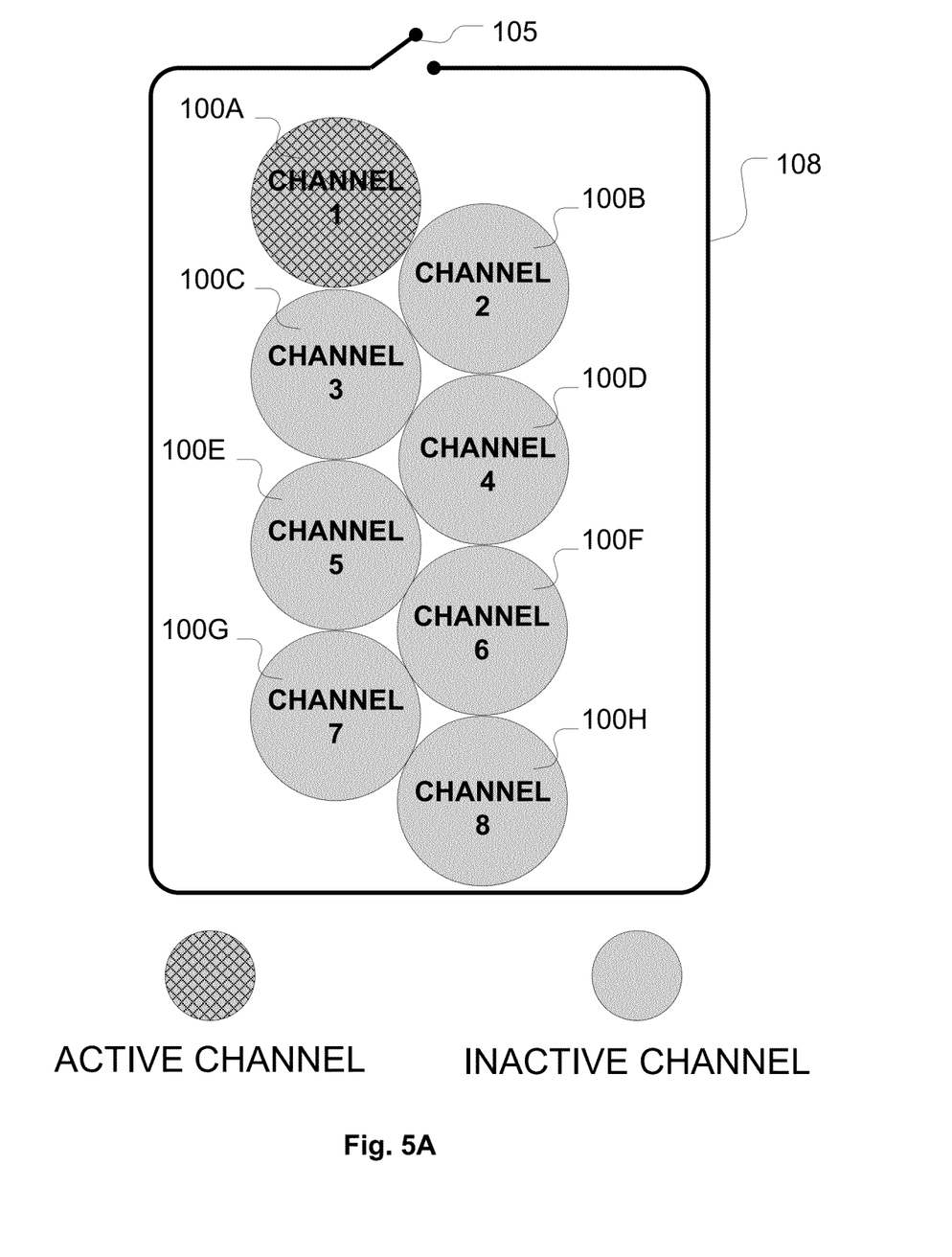
FIG. 5A shows multiple, non-simultaneously activated coils that are linked to a test loop.
Figure 5B:
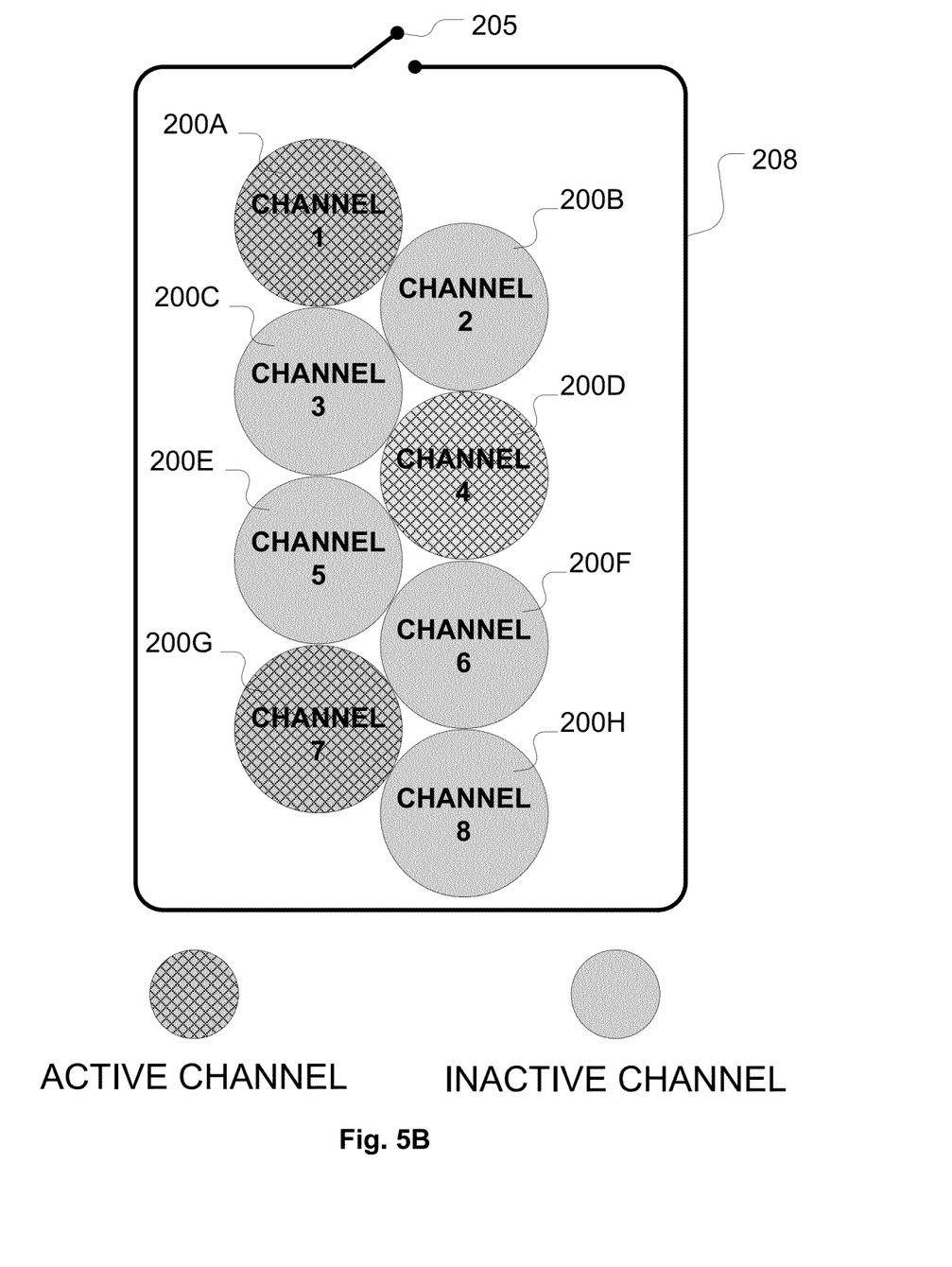
FIG. 5B shows an eddy current array with multiple, simultaneously activated coils that are linked to a test loop.
Figure 5C:
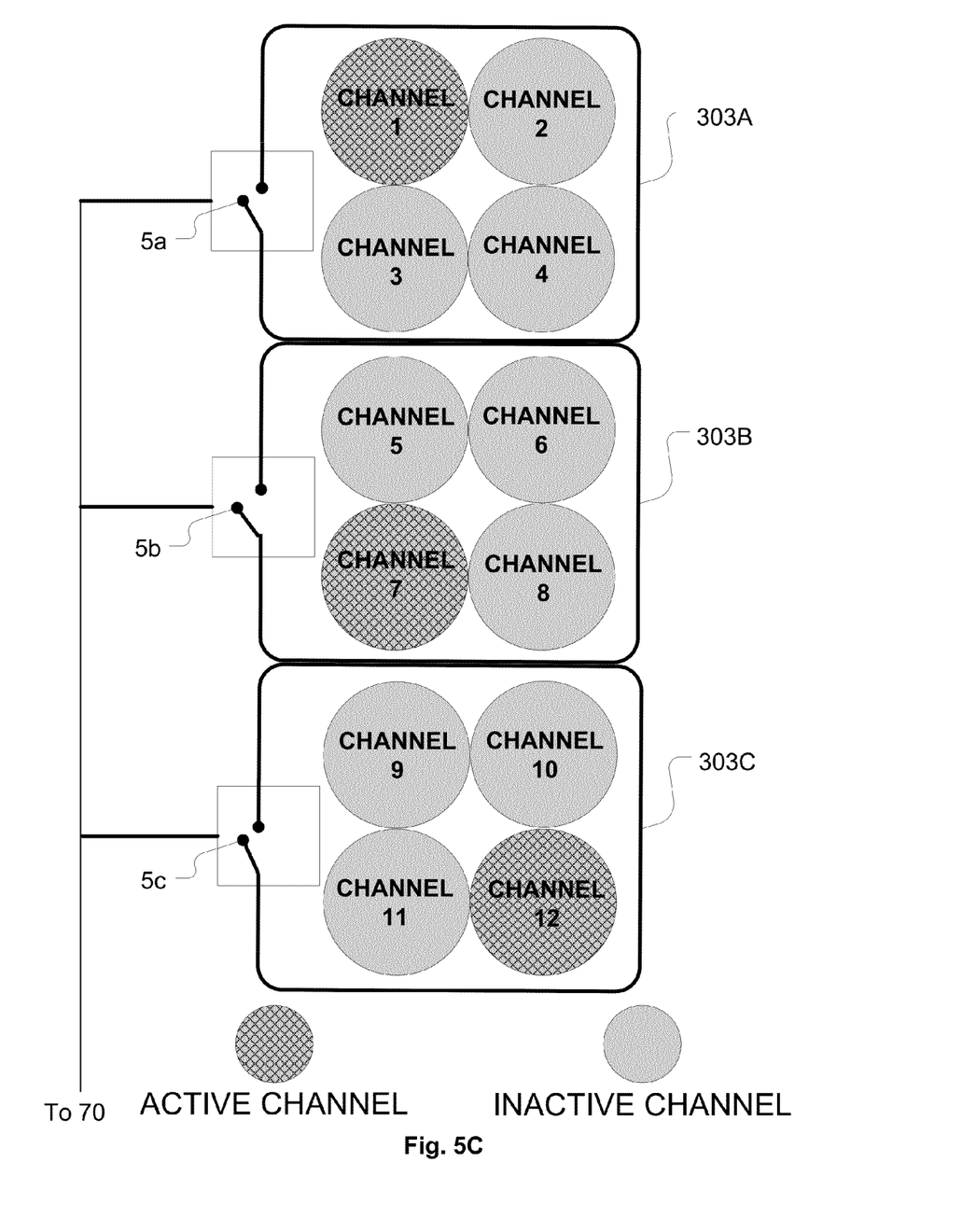
FIG. 5C shows an eddy current array with multiple, simultaneously activated coils, which are linked to multiple test loops.

Different configurations of channel activation in each time interval are presented in FIGS. 5A-5C. It should be understood that the individual channels presented in FIGS. 5A-5C can be any of the channel configurations previously presented in FIG. 1 or 3A. For the channel configuration corresponding to FIG. 3B, the test loop configuration will be adapted to separately affect differential receivers but otherwise the same concept applies.

Referring to FIG. 5A, eight (8) non-simultaneously activated channels 100A-100H are linked to the test loop 108. The same physical coil can be used on multiple channels without limiting to the scope of this embodiment of the invention as long as only one channel's driver coil is activated at each time interval. The activation of the test loop can be controlled by a switch 105. Referring to FIG. 5A, only channel 100A is activated for the illustrated time interval. In this case when a coil of a channel is broken or damaged, whether a driver or receiver coil, the TLA signal for the probe check evaluation will show an important PITV value. One can then conclude that the probe is functional in the system based on the PITV, relative to the damaged channel.

FIG. 5B shows an array of channels 200A-200H with multiple, simultaneously activated channels 200A, 200D, 200G, which are linked to test loop 208. Other channels are inactive during the time interval of this example. The activation of the test loop 208 can be controlled by a switch 205. In this example, when a driver coil of a channel does not work properly, and there is more than one activated driver channel in each time interval, the TLA signal will not be as informational as in the single channel activation of FIG. 5A, because eddy currents are still induced in the test loop by all other operational driver coils. The resulting PITV depends on the number of simultaneously activated channels. If the number of activated channels is such that the resulting PITV variation is close to observed tolerance during a normal operation, the broken coil detection will be difficult and multiple test loops are required (FIG. 5C).

When the number of channels with multiple, simultaneously activated channels increases in an array, multiple test loops could be required as shown in FIG. 5C. In this example there are three simultaneously activated test loops 303A, 303B, and 303C. As shown in the figure, in each test loop only one channel is activated at each time interval. In this case, each separated loop is equivalent to the FIG. 5A arrangement. When a coil of a channel in a test loop is damaged, the test loop generates a unique and readily recognizable PITV signature. Multiple test loops can all be connected to each other and can be activated simultaneously, which allows evaluating the integrity of the entire system.

As an alternative embodiment of the invention, one may use the inspection channels when the test loop is closed and monitor the system integrity when opening the loop. With this configuration, the test loop also acts as a shielding loop and can thus become an active and useful component for the inspection itself.

Although the present invention has been described in relation to particular embodiments thereof, many other variations and modifications and other uses will become apparent to those skilled in the art. It is preferred, therefore, that the present invitation be limited not by the specific disclosure herein, but only by the appended claims.

What is claimed is:

1. An eddy current object testing system, comprising:
    an eddy current probe array, configured for testing a test object, said eddy current probe array comprising more than two coils associated with different elements of more than two drive-sense channels;
    an acquisition unit coupled to the eddy current probe array for producing an impedance plane output for each of the channels, said acquisition unit is connected with each of the drive-sense channels; and
    at least one test loop provided on the eddy current probe array and at least one test loop switch in series with the at least one test loops, the at least one test loop switch being configured to selectively open or close the at least one test loops, to thereby cause the impedance plane output to assume a state that is indicative of a fault in one or more elements of the eddy current probe array; and
    wherein the acquisition unit is operative to selectively activate or deactivate selected ones of the drive-sense channels of the eddy current probe array.

2. The eddy current object testing system of claim 1, wherein the at least one test loop is integrated with the eddy current probe array in an EC probe housing.

3. The eddy current object testing system of claim 1, wherein the at least one test loop is provided physically separately from the eddy current probe array and is configured to be coupled to an existing EC probe.

4. The eddy current object testing system of claim 1, including a data processing and display unit electronically coupled to the EC acquisition unit and configured to display the EC output.

5. The eddy current object testing system of claim 1, wherein the at least one test loop is a single test loop.

6. The eddy current object testing system of claim 1, wherein each of the drive-sense channels comprises both a driver coil and a receiver coil.

7. The eddy current object testing system of claim 6, wherein the driver coil and the receiver coil are both substantially surrounded by the at least one test loop.

8. The eddy current object testing system of claim 1, wherein the impedance plane output is in the form of an impedance plane associated with an operation point.

9. The eddy current object testing system of claim 1, wherein each of the drive-sense channels comprises at least one driver coil and a pair of receiver coils which are configured as differential coils, and wherein the at least one test loop comprises a first test loop which overlaps a portion of the one of the receiver coils and a second test coil which overlaps the other one of the receiver coils.

10. The eddy current object testing system of claim 1, wherein each of the drive-sense channels is configured to produce the EC output indicative of a fault in the channel when the switch mechanism is in one of the status of being closed or open.

11. The eddy current object testing system of claim 1, wherein the processing and display unit is configured to produce the output indicative of a fault in the channel when the switch mechanism is in one of the status of being opened or closed.

12. The eddy current object testing system of claim 4 is further configured to produce a Probe Integrity Test Value (PITV) based on operation point shifts when the switching mechanism is activated.

13. The eddy current object testing system of claim 12, wherein the PITV is given by a vector ΔV, wherein $$\overrightarrow{\Delta V} = \frac{|\overrightarrow{V_1} - \overrightarrow{V_2}|}{|\overrightarrow{V_1}|}$$

wherein $V_1$ and $V_2$ are vectors in the impedance plane, $V_1$ is a reference vector for a fully functional eddy current probe array, and $V_2$ is a vector for a faulty eddy current probe array.

14. The eddy current object testing system of claim 1, wherein the channels are of multiple channels of the same type or different types and the at least one test loop is arranged to intersect with at least a portion of the magnetic field of each of the multiple channels.

15. The eddy current object testing system of claim 1, wherein the switch mechanism or the indicative of a fault takes place while the acquisition unit and the EC output are in a continuously operational mode.

16. The eddy current object testing system of claim 1, wherein the at least one test loop is a single test loop substantially surrounding the elements of the eddy current probe array with a single test loop switch in series therewith.

17. The eddy current object testing system of claim 1, wherein of the at least one test loop is a plurality of test loops which are provided with each test loop of said plurality of test loops comprising its respective test loop switch and encircling a respective group of the elements of the eddy current probe array.

18. A method of detecting a faulty eddy current testing channel in an eddy current probe having at least two drive-sense channels, the probe is electronically coupled with an acquisition unit, which is subsequently electronically coupled with a data processing and display unit, and the acquisition unit receiving an EC signal from the at least one channel and to generate an EC output representative of characteristics of the EC signal, the method comprising steps of:
providing at least one test loop substantially interacting with the at least one channel;
providing a switch mechanism in series with the at least one test loop, the switch is configured to be selectively opened or closed,
providing an alarm signal when the switch mechanism causes the output to assume a state that is indicative of a fault in the at least one drive-sense channel, and
selectively activating or deactivating selected ones of the drive-sense channels of the eddy current probe.

\* \* \* \* \*